US005334016A

United States Patent [19]

[11] Patent Number: 5,334,016
[45] Date of Patent: Aug. 2, 1994

Goldsmith et al.

[54] COMBINATION AIR ABRASIVE SYSTEM AND LASER SYSTEM FOR DENTAL APPLICATIONS

[75] Inventors: Daniel S. Goldsmith, West Bloomfield; William S. Parker, Ann Arbor, both of Mich.

[73] Assignee: American Dental Technologies, Inc., Troy, Mich.

[21] Appl. No.: 901,780

[22] Filed: Jun. 22, 1992

[51] Int. Cl.$^5$ .................... A61C 3/00

[52] U.S. Cl. .................... 433/29; 433/88; 433/142; 606/10

[58] Field of Search .................... 433/29, 88, 92, 142, 433/143, 101; 606/3, 10

[56] References Cited

U.S. PATENT DOCUMENTS

| | | | |
|---|---|---|---|
| 2,661,537 | 12/1953 | Angell | 32/58 |
| 2,969,049 | 12/1954 | Black | 32/58 |
| 3,890,712 | 6/1975 | Lopez | 433/92 |
| 3,971,375 | 7/1976 | Hill | 128/173 |
| 4,252,054 | 2/1981 | Bakels | 433/92 |
| 4,276,023 | 6/1981 | Phillips et al. | 433/85 |
| 4,494,932 | 1/1985 | Rzewinski | 433/88 |
| 4,523,911 | 6/1985 | Braetsch et al. | 433/101 |
| 4,635,897 | 1/1987 | Gallant | 251/5 |
| 4,708,534 | 11/1987 | Gallant | 406/75 |
| 4,767,404 | 8/1988 | Renton | 604/48 |
| 4,797,098 | 1/1989 | Kawata | 433/101 |
| 4,826,431 | 5/1989 | Fujimura et al. | 433/29 |
| 4,872,837 | 10/1989 | Issalene et al. | 433/29 |
| 4,893,440 | 1/1990 | Gallant et al. | 51/436 |
| 4,992,047 | 2/1991 | Warner | 433/29 |
| 5,120,219 | 6/1992 | De Farcy | 433/88 |
| 5,147,203 | 9/1992 | Seidenberg | 433/29 |
| 5,178,536 | 1/1993 | Werly et al. | 433/29 |
| 5,194,005 | 3/1993 | Levy | 433/29 |

*Primary Examiner*—Robert P. Swiatek
*Assistant Examiner*—Todd E. Manahan
*Attorney, Agent, or Firm*—Gifford, Groh, Sprinkle, Patmore and Anderson

[57] ABSTRACT

A combination air abrasive system and laser system are provided for dental applications. The air abrasive system creates an abrasive material laden gas flow and then directs this gas flow towards a target site in the patient's mouth. The air abrasive system also includes a vacuum system which creates an air flow to remove the abrasive material after impingement on the target site. The abrasive material is filtered from the air flow and the resulting clean air is then used to create a positive pressure within the housing for the dental laser system to prevent the entry of debris and other contaminants within the laser system. Additionally, the clean air flow is used to clean the lens system for the laser. Also, the air abrasive system and laser system include a common control system and may also utilize a common aiming and illumination mechanism. Further, the combination unit has a common light source that not only illuminates the target area, but can be used as a curing light for dental materials, which light source may or may not be a laser. Further, the combination unit has a single common footswitch that allows the performance of more than one task.

24 Claims, 1 Drawing Sheet

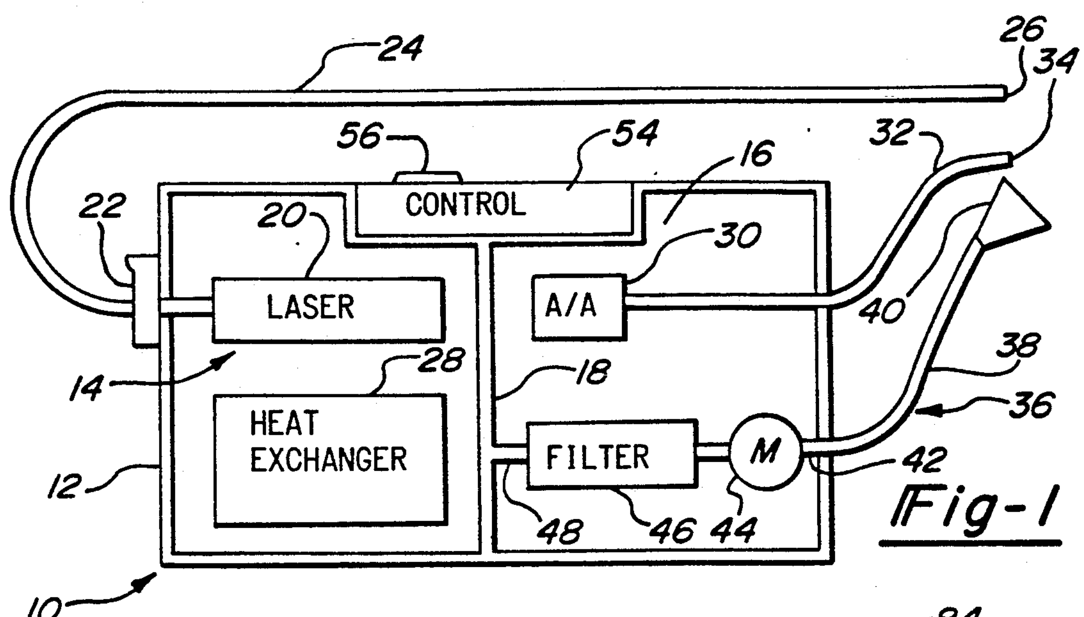
Fig-1
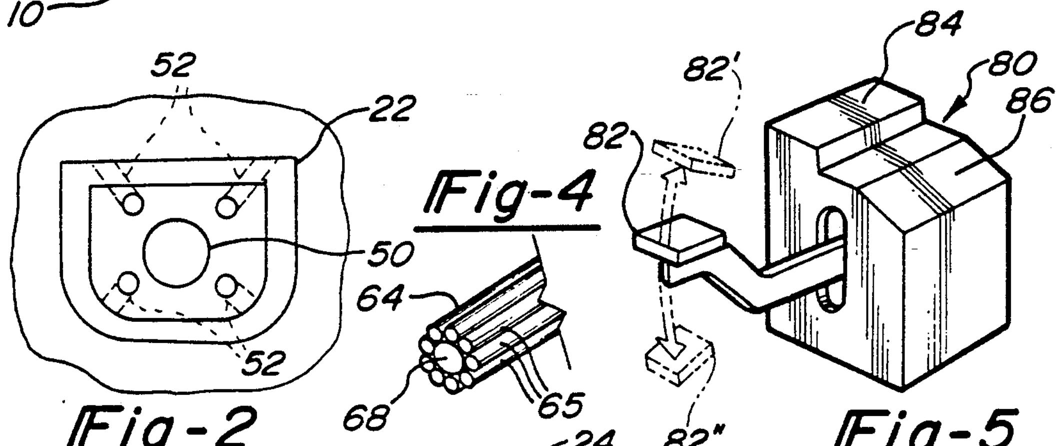
Fig-2
Fig-4
Fig-5
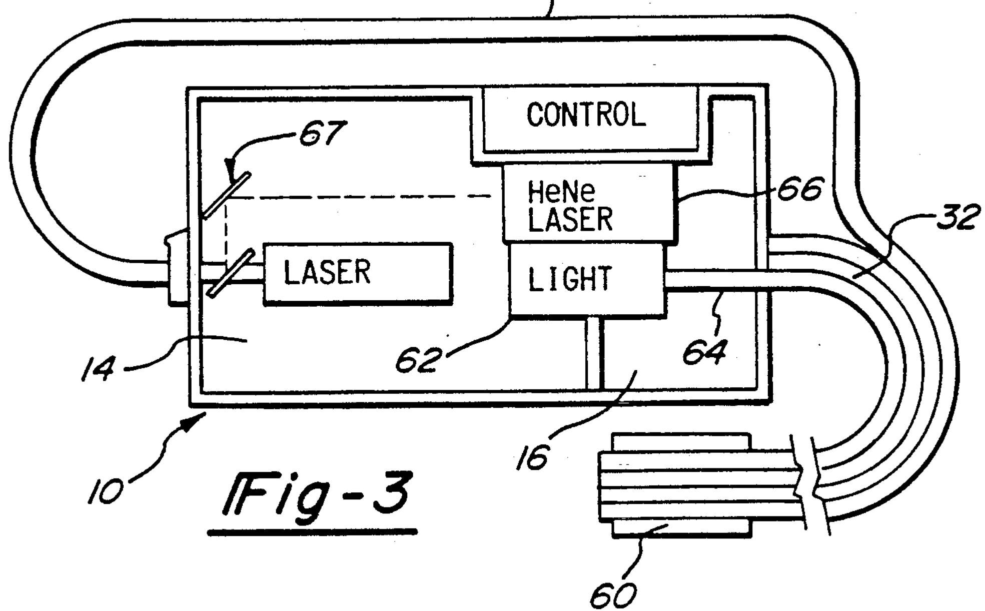
Fig-3

COMBINATION AIR ABRASIVE SYSTEM AND LASER SYSTEM FOR DENTAL APPLICATIONS

BACKGROUND OF THE INVENTION

I. Field of the Invention

The present invention relates to a combination air abrasive system and laser system for dental applications.

II. Description of the Prior Art.

Laser systems are becoming increasingly more common in dental offices for use in a number of dental procedures Such laser systems typically comprise a housing which contains the laser which generates a laser output to an output port on one side of the housing. This output port includes a lens while an optical fiber delivery system coupled to the lens receives the laser output from the laser and delivers the laser output to a target area in the patient's mouth.

Likewise, there have been previously known air abrasive systems for dental applications. Such air abrasive systems include means for creating an abrasive material laden gas flow and then directing this gas flow towards a target site in the patient's mouth. The abrasive material, once it impinges upon the target site eradicates tooth structure, including enamel, or could function with a different type of abrasive material that would not remove the enamel, but rather, would remove stains and the like, and by using lower air pressure settings between 20 PSI and 60 PSI, the air abrasive system could function as a dental device to clean teeth rather than remove tooth structure. The use of an abrasive system to clean teeth is also previously known, but not in combination. In addition, lasers have been used to cure dental materials before but never have been known to be used in combination with an air abrasive system where it also functions as a source of illumination for the air abrasive activities. Further, a single footswitch controlling the speed of a dental drill with various positions has been known in dentistry but has not been used for an air abrasive system with various settings, nor has it been used in combination with a vacuum system and/or illuminating light and/or a combination air abrasive system and a laser.

After the abrasive material impinges upon the target site, a vacuum system for the air abrasive system evacuates the abrasive material from the patient's mouth after impingement on the target site. The removed abrasive material is then filtered and the resulting clean air is typically exhausted to the atmosphere.

There have been no previously known combination air abrasive systems and laser systems for dental applications. Furthermore, such a combination would be highly advantageous since the air abrasive systems are capable of performing certain procedures while the laser is capable of performing other procedures. Together the air abrasive unit and laser system can perform a wide range of dental procedures.

Although it is possible to have an independent air abrasive system and an independent dental laser system in the dental office, such a solution is disadvantageous in a number of different respects. For example, the independent laser system and air abrasive system are relatively expensive to obtain. Furthermore, independent laser and air abrasive systems have previously utilized independent aiming systems, illumination systems, handpieces, activation footswitches and other activation devices and thus add to the overall clutter and complexity of the dental office.

SUMMARY OF THE PRESENT INVENTION

The present invention provides a combination air abrasive system and laser system for dental applications which overcomes the above mentioned disadvantages of the previously known devices.

In brief, the combination air abrasive system and laser system of the present invention comprises a housing in which both the air abrasive system and laser system are contained. A wall within the housing, however, separates the operating components of the laser system from the abrasive system.

The abrasive system also includes a vacuum means which removes grit from the patient's mouth after impingement of the grit on the target site. This removed grit is filtered and the resulting clean air is then used to create a positive pressure in the laser housing. The positive pressure in the laser housing prevents contaminants dirt and other debris from entering into the interior of the laser housing.

Additionally, the laser system includes an output port having a lens. The optical delivery system for the laser is selectively connected to the output port during use of the laser system. In order to prevent dirt lint and other debris from accumulating on the port lens, a plurality of air ducts are provided in the laser housing so that air flow outwardly through these ports impinge upon the lens and clean the lens. The positive pressure within the interior of the laser housing creates this lens cleaning air flow.

Preferably, both the air abrasive system and the laser system utilize a common control system for controlling operation of both the laser and the air abrasive unit. Preferably the control system includes an external keypad for user entry of the desired function, as well as a microprocessor for controlling the operation of both the laser and the air abrasive unit.

A common illuminating means can also be employed for illuminating the target site or target area for both the air abrasive unit as well as the laser system. In the preferred embodiment of the invention, this illumination means comprises a lamp contained in the combination housing and an optical fiber assembly which delivers the illumination from the lamp to the target site or target area. In addition, certain types of lasers in the blue range can be used for the function of a curing light for dental materials and other dental applications, as well as the source of illumination for the air abrasive system.

Similarly, the air abrasive system and laser system employ a common aiming means for aiming the output from the laser system, as well as the abrasive material laden gas flow from the air abrasive system, to the target site or target area. In a preferred form of the invention, this aiming means comprises a continuous wave laser having a laser output in the visible range. A helium-neon laser is used as the aiming laser.

Additionally, a common handpiece is preferably used for both the air abrasive system as well as the laser system. This is particularly true where a common illumination and/or aiming means is employed for both the laser system and air abrasive system.

BRIEF DESCRIPTION OF THE DRAWING

A better understanding of the present invention will be had upon reference to the following detailed description when read in conjunction with the accompanying drawing, wherein like reference characters refer to like parts throughout the several views and in which:

FIG. 1 is a diagrammatic view illustrating a preferred embodiment of the present invention;

FIG. 2 is a fragmentary view of the laser output port and enlarged for clarity;

FIG. 3 is a view similar to FIG. 1 but illustrating a modification thereof;

FIG. 4 is a fragmentary view illustrating a preferred embodiment of the illuminating and aiming means of the present invention; and FIG. 5 is a view of a foot pedal control for the preferred embodiment of the present invention.

DETAILED DESCRIPTION OF A PREFERRED EMBODIMENT OF THE PRESENT INVENTION

With reference first to FIG. 1, a preferred embodiment of the combination air abrasive system and laser system 10 of the present invention is thereshown and comprises a housing 12 containing the laser system 14 and air abrasive system 16. A housing wall 18 separates the laser system 14 from the air abrasive system 16 and forms a laser housing and an air abrasive housing.

The laser system 14 includes a laser 20 having its output optically coupled to a port 22 on the exterior of the housing 12. An optical fiber delivery system 24 is then selectively connected to the port 22 so that the fiber 24 delivers the radiation from its distal end 26. Since the optical fiber system 24 is flexible, the distal end 26 delivers the laser radiation to the desired target area in a patient's mouth.

The laser system 14 further includes a heat exchanger 28 for removing heat from the laser system 14. Such heat exchangers 28 are conventional in construction and remove the heat typically caused by flash lamps used to excite the laser 20.

The air abrasive system 16 includes means 30 for creating an abrasive material laden gas flow as well as a conduit 32 for delivering the abrasive material laden gas flow through a distal end 34 of the conduit 32. The conduit 32 is flexible so that the abrasive material laden gas flow can be selectively delivered by the dentist to the desired target site in the patient's mouth.

The air abrasive system 16 further includes a vacuum system 36 for removing the abrasive material, i.e. grit, from the patient's mouth after impingement of the grit on the target site. This vacuum system 36 comprises an elongated conduit or hose 38 having a mouthpiece 40 positioned adjacent the patient's mouth and its other end 42 connected to a vacuum motor 44. The mouthpiece 40 is detachably secured to the vacuum hose 38 and is preferably disposed of after use on a single patient. Thus, when activated, the motor 44 inducts air together with entrained grit through the tube 38 and to the vacuum motor 44. The motor 44 then passes this grit through a filter 46 which removes the grit from the air flow From the filter 46, the now clean air is communicated by a conduit 48 to the housing for the laser system 14. In doing so, a positive pressure is contained within the laser housing which prevents the entry of dirt, debris and other contaminants into the laser housing.

Preferably, a portion of the clean air flow from the filter 48 is directed directly upon the heat exchanger 28 for the laser system 14 thus eliminating the previously known necessity of a separate cooling fan for the heat exchanger 28.

With reference now especially to FIG. 2, the laser output port 22 is thereshown in greater detail and comprises a lens 50 which is optically coupled to the laser 20. It is important that the lens 50 be kept clear of dust and other debris for optimal transmission of the laser radiation to the target area Therefore in the preferred embodiment of the invention, a plurality of air ducts 52 are provided through the laser housing so that air flow through the air ducts 52 impinge upon and clean the lens 50. Furthermore, the positive air pressure created by the vacuum motor 44 of the air abrasive system 16 creates the desired air flow through the ducts 52.

Referring again to FIG. 1, preferably a common control 54 is provided for both the laser system 14 and air abrasive system 16. This control 54 includes an external keypad 56 for user entry of the desired commands. The control 54 is also preferably microprocessor based.

With reference now to FIGS. 3 and 4, a modification the combination laser system and air abrasive system 10 of the present invention is thereshown in which both the optical fiber delivery system 24 for the dental laser system 14, as well as the conduit 32 for the air abrasive system 16 are bound together and delivered to a single handpiece 60.

The combination unit 10 includes a common light source 62 while light from the light source 62 is delivered by an optical fiber assembly 64 to the handpiece 60. As such, the common illumination means 62 can be used to illuminate the target site for both the air abrasive unit as well as the laser system.

The light 62, in addition to illuminating the target site, can also be used to cure composites. For example, a laser, such as an argon laser, can be used as the light source 62 to both illuminate the target site as well as cure certain composites. Such an argon laser could also be used for dental therapeutic procedures.

Similarly, an aiming means 66 is provided for aiming both the air abrasive unit 16 and the laser system 14 In the preferred form of the invention, the aiming means 66 comprises a continuous wave laser which lases within the visible range, such as a helium-neon laser, and the laser output is delivered to the handpiece 60 via a beam splitter 68 to the optical fiber 24.

With reference now to FIG. 4, a preferred embodiment of the optical fiber assembly 64, together with the optical fiber 68 is thereshown. The optical fiber assembly 64 comprises a plurality of individual optical fibers 65 arranged in a circular bundle around the optical fiber 68 for the aiming means 66. Other arrangements, however, can alternatively be used.

With reference to FIG. 5, a foot pedal assembly 80 is preferably used to control activation of the combination unit 10. The foot pedal assembly includes a foot lever 82 movable between a high position, indicated at 82', a low position, indicated at 82" and a medium position, indicated in solid line. Different positions of the foot lever 82 would, of course, cause different activation of the combination unit.

The foot pedal assembly 80 also includes two or more switches 84 and 86 which control various functions of the combination unit 10 For example one switch 84 can be used to activate the vacuum motor 44 while the second switch 86 can be used to activate the light source 62 laser and/or the air abrasive unit.

From the foregoing, it can be seen that the present invention provides a novel combination air abrasive system and laser system for dental applications.

Having described our invention, however, many modifications thereto will become apparent to those skilled in the art to which it pertains without deviation from the spirit of the invention as defined by the scope of the appended claims.

We claim:

1. In combination:

an air abrasive system for dental applications comprising means for creating an abrasive material laden gas flow, means for directing said gas flow toward a target site in a patient's mouth, means for creating an air flow to remove abrasive material after impingement on the target sight and means for filtering abrasive material from said air flow to create a clean air flow, and a laser system for dental applications comprising a housing containing a laser, means for exciting said laser to generate a laser output and means for delivering said laser output to a target area in a patient's mouth, and means for fluidly communicating said clean air flow to said laser housing so that said clean air flow creates a positive pressure in said laser housing.

2. The invention as defined in claim 1 wherein said laser system comprises a heat exchanger contained in said laser housing.

3. The invention as defined in claim 1 wherein said means for delivering said laser output comprises a lens secured to said housing so that one side of said lens faces exteriorly of said housing, and comprising at least one opening in said housing adjacent said lens, whereby positive air pressure in said housing flows outwardly through said at least one opening to clean said exteriorly facing side of said lens.

4. In combination:

an air abrasive system for dental applications comprising a housing containing said air abrasive system, means for creating an abrasive material laden gas flow and means for directing said gas flow toward a target site in a patient's mouth, a laser system for dental applications comprising said housing also containing a laser, means for exciting said laser to generate a laser output and means for delivering said laser output to a target area in a patient's mouth, and common means for controlling both said air abrasive system and said laser system.

5. The invention as defined in claim 4 wherein said controlling means comprises a microprocessor.

6. The invention as defined in claim wherein said common controlling means comprises a foot pedal assembly.

7. In combination:

an air abrasive system for dental applications comprising a housing containing said air abrasive system, means for creating an abrasive material laden gas flow and means for directing said gas flow toward a target site in a patient's mouth, a laser system for dental applications comprising said housing containing a laser, means for exciting said laser to generate a laser output and means for delivering said laser output to a target area in a patient's mouth, and means for illuminating said target site and said target area.

8. The invention as defined in claim 7 wherein said illuminating means comprises a source of illumination and means for selectively delivering light from said source to either said target area or said target sight.

9. The invention as defined in claim 8 wherein said source of illumination comprises a laser.

10. The invention as defined in claim 7 wherein said means for delivering said laser output comprises an optical fiber.

11. In combination:

an air abrasive system for dental applications comprising a housing containing said air abrasive system, means for creating an abrasive material laden gas flow and means for directing said gas flow toward a target site in a patient's mouth, a laser system for dental applications comprising said housing also containing a laser, means for exciting said laser to generate a laser output and means for delivering said laser output to a target area in a patient's mouth, and means for selectively aiming said abrasive material laden gas flow or said laser output.

12. The invention as defined in claim 11 wherein said aiming means comprises means for generating a visible laser beam and means for delivering said laser beam to said target site or said target area.

13. The invention as defined in claim 12 wherein said means for generating a visible laser beam comprises a helium-neon laser.

14. The invention as defined in claim 13 wherein said means for delivering said laser beam to said target site or target area comprises an optical fiber.

15. In combination:

an air abrasive system for dental applications comprising a housing containing said air abrasive system, means for creating an abrasive material laden gas flow and means for directing said gas flow toward a target site in a patient's mouth, a laser system for dental applications comprising said housing also containing a laser, means for exciting said laser to generate a laser output and means for delivering said laser output to a target site in a patient's mouth, and means for illuminating said target site with said laser and means for supplying curing materials to said target site.

16. The invention as defined in claim 15 wherein said laser is an argon laser.

17. In combination:

an air abrasive system for dental applications comprising a housing containing said air abrasive system: means for creating an abrasive material laden gas flow and means for directing said gas flow toward a target site in a patient's mouth, a laser system for dental applications comprising said housing also containing a laser, means for exciting said laser to generate a laser output and means for delivering said laser output to a target area in a patient's mouth, and means for controlling said air abrasive system and said laser system comprising a foot pedal assembly.

18. The invention as defined in claim 17 wherein said laser system further comprises an illuminating light and wherein said foot pedal assembly controls activation of said light.

19. The invention as defined in claim 18, wherein said foot pedal assembly only has an activation position.

20. The invention as defined in claim 18, wherein said foot pedal assembly only has a neutral position.

21. In combination:

an air abrasive system for dental applications comprising means for creating an abrasive material laden gas flow, means for directing said gas flow toward a target site in a patient's mouth, a laser system for dental applications comprising a housing containing a laser, means for exciting said laser to generate a laser output and means for delivering said laser output to a target area in a patient's mouth, and means for illuminating said target site with a light and means for supplying curing materials to said target site.

22. In combination:

an air abrasive system for dental applications comprising means for creating an abrasive material laden gas flow, means for directing said gas flow toward a target site in a patient's mouth and a vacuum system for removing grit after impingement on the target site, a laser system for dental applications comprising a housing containing a laser, means for exciting said laser to generate a laser output and means for delivering said laser output to a target area in a patient's mouth, and means for controlling said air abrasive system and said laser system comprising a foot pedal assembly, said foot pedal assembly controlling activation of said vacuum system.

23. The invention as defined in claim 22 wherein said foot pedal assembly comprises a foot lever having at least two different positions which selectively control activation of the air abrasive system, the laser system and the vacuum system.

24. The invention as defined in claim 23 wherein said foot lever has a neutral position and an activation position.

* * * * *